United States Patent
Lindenblatt et al.

(10) Patent No.: US 7,262,165 B2
(45) Date of Patent: Aug. 28, 2007

(54) AQUEOUS PREPARATION CONTAINING OLIGOPEPTIDES AND ETHERIFIED CYCLODEXTRIN

(75) Inventors: Hiltrud Lindenblatt, Egelsbach (DE); Hans-Peter Zobel, Floersheim (DE)

(73) Assignee: Merck Patent GmbH, Darmstadt (DE)

( * ) Notice: Subject to any disclaimer, the term of this patent is extended or adjusted under 35 U.S.C. 154(b) by 125 days.

(21) Appl. No.: 10/518,924

(22) PCT Filed: May 19, 2003

(86) PCT No.: PCT/EP03/05224

§ 371 (c)(1), (2), (4) Date: Dec. 23, 2004

(87) PCT Pub. No.: WO04/000344

PCT Pub. Date: Dec. 31, 2003

(65) Prior Publication Data

US 2005/0239692 A1    Oct. 27, 2005

(30) Foreign Application Priority Data

Jun. 24, 2002   (DE) .............................. 102 28 049

(51) Int. Cl.
*A61K 38/12* (2006.01)
(52) U.S. Cl. ...................................................... 514/11
(58) Field of Classification Search ...................... None
See application file for complete search history.

(56) References Cited

U.S. PATENT DOCUMENTS 5,376,632 A    12/1994  Konings et al.
6,001,961 A    12/1999  Jonczyk et al.

FOREIGN PATENT DOCUMENTS

| WO | WO8502767 | 7/1985 |
|----|-----------|--------|
| WO | WO9111200 | 8/1991 |
| WO | WO 0062793 | 10/2000 |

OTHER PUBLICATIONS

Kamm, W. et al: "Evaluation of Absorption Enhancement for a Potent Cyclopeptidic.Alpha..Nu..Beta.3-Antagonist in a Human Intestinal Cell Line (CACO-2)" European Journal of Pharmaceutical Sciences (2000), 10(3), 205-214, Seite 206, Linke Spalte, Letzter Absatz; Seite 208, Linke Spalte, Absatz 3; Seite 213, Linke Spalte, Absatz 2-Absatz 3.

Johnson, M.D. et al., "Solubilization of tripeptide HIV protease inhibitor using a combination of ionization and complexation with chemically modified cyclodextrin," Journal of Pharm. Sci., Aug. 1994, pp. 1142-1146 (abstract).

*Primary Examiner*—Cecilia J. Tsang
*Assistant Examiner*—Christina Marchetti Bradley
(74) *Attorney, Agent, or Firm*—Millen, White, Zelano, Branigan, P.C.

(57) ABSTRACT

The present invention relates to an aqueous pharmaceutical preparation of oligopeptides comprising an oligopeptide of the formula I, cyclo-(n-Arg-nGly-nAsp-nD-nE), and a partially etherified β-cyclodextrin having a water solubility of greater than 1.8 mg/ml of water, and to the preparation of the aqueous pharmaceutical preparation.

23 Claims, No Drawings

AQUEOUS PREPARATION CONTAINING OLIGOPEPTIDES AND ETHERIFIED CYCLODEXTRIN

The present invention relates to an aqueous pharmaceutical preparation of oligopeptides of the formula I, comprising an oligopeptide and an etherified β-cyclodextrin having a water solubility of greater than 1.8 mg/ml of water, and to the preparation of the aqueous pharmaceutical preparation.

The oligopeptides present in the preparation according to the invention are cyclopeptides of the formula I

in which
D and E each, independently of one another, denote Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homoPhe, Phg, Pro, Pya, Ser, Thr, Tia, Tic, Trp, Tyr or Val, where the said amino acid radicals may also be derivatised,
R denotes alkyl having 1-18 C atoms,
Hal denotes F, Cl, Br or I,
Ac denotes alkanoyl having 1-10 C atoms, aroyl having 7-11 carbon atoms or aralkanoyl having 8-12 C atoms,
n denotes a hydrogen atom or an alkyl radical R, benzyl or an aralkyl radical having 7-18 C atoms on the alpha-amino function of the corresponding amino acid radical,
with the proviso that at least one amino acid radical has a substituent n, where n denotes R, and where, if they are radicals of optically active amino acids and amino acid derivatives, both the D and L forms are included, and physiologically acceptable salts thereof.

The oligopeptides of the formula I are described in EP 0 770 622 A2. Regarding the significance of the amino acids and substituents present in the formula I and the preparation of the peptides, reference is made to this specification.

The oligopeptides of the formula I act as integrin inhibitors, inhibiting, in particular, the interactions of the β$_3$- or β$_5$-integrin receptors with endogenous ligands. The compounds exhibit an activity against the integrins α$_v$β$_3$, α$_v$β$_5$, α$_v$β$_6$ and α$_{II}$β$_3$, but also against α$_v$β$_1$ and α$_v$β$_8$ receptors. Blockage of the α$_v$β$_3$ and α$_v$β$_6$ receptors is of particular importance here. Prevention of the stimulation of α$_v$β$_3$ receptors by the endogenous ligand fibrinogen should be mentioned in particular here.

The interactions described result, in particular, in inhibition of angiogenesis, making the oligopeptides suitable for cancer therapy. Particular mention should be made here of the oligopeptide cilengitide, a cyclic pentapeptide with the chemical designation cyclo-(Arg-Gly-Asp-D-Phe-NMe-Val). Cilengitide is already in phase II of clinical trials for the treatment of cancer diseases.

Like other peptides, the oligopeptides of the formula I are also preferably administered parenterally as an aqueous solution. For them to be used therapeutically, aqueous solutions of the oligopeptides are therefore necessary. The aqueous oligopeptide solutions employed for this purpose should be matched to the particular therapy requirements, in particular they should comprise the active ingredient in the amount necessary therapy and should have an adequate shelf life.

The treatment of tumour diseases requires parenteral administration of relatively large amounts of active ingredient. Owing to their peptide structure, the oligopeptides have relatively good water solubility. Nevertheless, the relatively large amounts of active ingredient necessary for the therapy result in relatively large volumes of active ingredient solution which are to be administered parenterally. These can then no longer simply be injected, but instead must be infused.

Cilengitide, for example, has a saturation solubility in physiological saline solution of about 19 mg/ml and can therefore, for therapeutic use, be safely administered parenterally in a concentration of 15 mg/ml dissolved in physiological saline solution. If, for example, a dose of 1500 mg is necessary for therapy with cilengitide, a volume to be administered of 100 ml arises. Volumes in this order of magnitude can no longer simply be injected and must be infused, which is disadvantageous.

In order to reduce the respective volume of active ingredient solution to be administered, it is desirable to increase the active ingredient content in the respective aqueous solution. Like other peptides, the solubility of the oligopeptides is dependent on the pH of the respective solvent. A suitable solubility-increasing measure is therefore, in particular, adjustment of the pH of the aqueous solvent to a value at which the oligopeptide has higher solubility. However, the pH values necessary for this purpose are in a non-physiological range, which is to be regarded as extremely critical with respect to parenteral administration. Furthermore, a pH which differs greatly from the physiological pH usually results in accelerated peptide degradation in aqueous solution, meaning that solutions of this type also have an inadequate shelf life.

Extensive attempts to increase the solubility of oligopeptides have not achieved the desired success. For example, it has unsuccessfully been attempted to improve the solubility of cilengitide by addition of physiologically tolerated organic solvents, such as ethanol or propanediol. The addition of surfactants, such as Cremophor and polysorbate 80, likewise did not produce any significant improvement in the solubility of cilengitide.

Although mixtures of citric acid, phosphate buffer and surfactants enabled the solubility of cilengitide to be increased, these solutions were, however, not stable on storage.

EP 0149 197 discloses that cyclodextrin ethers are able to increase the water solubility of sparingly water-soluble medicaments. Inclusion compounds are said to be formed here, with the medicaments penetrating into the hydrophobic cavity of the cyclodextrin ring system. A prerequisite for the ability of the medicaments into the cavity is that they also fit into the cavity. The medicaments must therefore also not exceed a certain spatial size. All the medicaments mentioned in EP 0 149 197 are low-molecular-weight chemical compounds and have low solubility in water. By contrast, the active ingredients in question are peptides which have relatively good solubility in water and in addition have a comparatively high molecular weight and consequently a relatively large spatial size.

The object of the present invention was therefore to provide an aqueous preparation having an increased content of oligopeptides of the formula I which is suitable for parenteral administration. The preparation should not comprise any toxicologically unacceptable adjuvants and should be stable over a relatively long time.

Surprisingly, a preparation which meets these requirements has been found in the form of a solution which, besides an oligopeptide of the formula I, comprises a β-cyclodextrin ether having a water solubility of greater than 1.8 mg/ml.

The preparation according to the invention can be stored for a period of at least 6 months in a stable manner at refrigerator temperature (2-8° C.) and even at room temperature (25° C., 60% r.h.). Surprisingly, the preparation according to the invention can also be stored in a stable manner at elevated temperatures and atmospheric humidity levels, for example for 3 months at a temperature of 30° C., 60% r.h. and for 4 weeks at 40° C. and 75% r.h.

β-Cyclodextrin is an α1,4-linked cyclic oligosaccharide comprising 7 glucose units which has a saturation solubility of 1.8 mg/ml in water at room temperature. Each of the (anhydro)glucose units of β-cyclodextrin contains free hydroxyl groups in the 2-, 3-, and 6-position, each of which may be etherified. If all or some of the free hydroxyl groups on the glucose units are etherified with alkyl groups containing one or more polar, i.e. readily water-soluble group (s), such as, for example, a hydroxyalkyl group, etherified β-cyclodextrins having increased water solubility compared with pure β-cyclodextrin are formed. Suitable hydroxyalkyl groups which increase the water solubility are, for example, hydroxyethyl or hydroxypropyl groups, which can be introduced into the β-cyclodextrin by reaction of the β-cyclodextrin with the corresponding alkylene oxides, such as ethylene oxide or propylene oxide.

The ether substituents present are preferably hydroxyethyl and/or hydroxypropyl groups.

The aqueous pharmaceutical preparation preferably comprises partially etherified β-cyclodextrin, i.e. β-cyclodextrin in which only some of the hydroxyl groups of the anhydroglucose units are in etherified form.

Depending on the amount of alkylene oxide employed for the etherification in relation to the β-cyclodextrin, etherified β-cyclodextrins having different degree of substitution are formed. The degree of substitution based on ether substitution is expressed below as the molar degree of substitution (MS) and denotes the molar amount of alkylene oxide employed per mole of (anhydro)glucose unit.

In accordance with the invention, the partially etherified β-cyclodextrins present in the aqueous pharmaceutical preparation have a molar degree of substitution of between 0.2 and 10. Preference is given to etherified β-cyclodextrins having a molar degree of substitution of between 0.2 and 2, particularly preferably having a molar degree of substitution of between 0.5 and 0.8 and very particularly preferably having a molar degree of substitution of about 0.58-0.73.

The oligopeptide present in the aqueous solution according to the invention can be any of the oligopeptides covered by the above general formula I. The oligopeptide present in the aqueous pharmaceutical preparation is preferably cyclo-(NMeArg-Gly-Asp-D-Phe-Val), cyclo-(Arg-Gly-Asp-DPhe-NMeVal), cyclo-(Arg-NMeGly-Asp-DPhe-Val), cyclo-(Arg-Gly-NMeAsp-DPhe-Val) or cyclo-(Arg-Gly-Asp-NMeDPhe-Val). Cilengitide is particularly preferably present. As already mentioned above, cilengitide has the chemical designation cyclo-(Arg-Gly-Asp-D-Phe-NMe-Val).

If the aqueous preparation is not already isotonic due to the osmotic properties of the oligopeptide and due to the cyclodextrin, an isotonicity agent, preferably a physiologically tolerated salt, such as, for example, sodium chloride or potassium chloride, or a physiologically tolerated polyol or a sugar, such as, for example, glucose or glycerol or mannitol, may furthermore be present in an amount necessary for establishing isotonicity.

Furthermore, the aqueous preparation according to the invention may comprise further physiologically tolerated adjuvants, such as, for example, antioxidants, such as ascorbic acid or glutathione, preservatives, such as phenol, m-cresol, methyl- or propylparaben, chlorobutanol, thiomersal or benzalkonium chloride, or further stabilisers, structure formers and solubilisers, such as polyethylene glycols (PEG), for example PEG 3000, 3350, 4000 or 6000, or dextrans.

In addition, the aqueous preparation according to the invention may comprise buffers, where it is in principle possible for all physiologically tolerated substances which are suitable for setting the desired pH to be employed. Any buffer substance present is present in a concentration of from 5 mmol/l to 50 mmol/l, preferably in a concentration of from 10 to 20 mmol/l. Preferred buffers are citrate buffer or phosphate buffer. Suitable phosphate buffers are solutions of the mono- and/or disodium and potassium salts of phosphoric acid, such as disodium hydrogenphosphate or potassium dihydrogenphosphate, and mixtures of the sodium and potassium salts, such as, for example, mixtures of disodium hydrogenphosphate and potassium dihydrogenphosphate.

The aqueous preparation advantageously has a pH of from 5 to 8, preferably a pH of from 5.6 to 7.4, particularly preferably a pH of from 6 to 7.2. The osmolality is preferably from 250 to 350 mOsmol/kg. The aqueous preparation can thus be administered directly intravenously or intraarterially substantially without pain.

According to a preferred embodiment of the invention, the aqueous pharmaceutical preparation comprises from 20 to 120 mg/ml of cilengitide and from 15 to 25% by weight of hydroxypropyl-β-cyclodextrin having a molar degree of substitution of from 0.5 to 0.8.

According to a particularly preferred embodiment of the invention, the aqueous pharmaceutical preparation comprises about 80 mg/ml of cilengitide and about 20% by weight of 2-hydroxypropyl-β-cyclodextrin having a molar degree of substitution of about 0.58-0.73.

The aqueous preparation can be prepared by dissolving the substances present in the preparation successively in water. In an advantageous manner, firstly the cyclodextrin ether is dissolved in water, and the oligopeptide and any further adjuvants are subsequently added. The invention therefore also relates to a process for the preparation of the aqueous pharmaceutical preparation according to the invention which is characterised in that firstly the β-cyclodextrin ether is dissolved in water, and the active ingredient and any further adjuvants are subsequently added.

If necessary, the solution comprising the particular oligopeptide, the β-cyclodextrin ether and any further adjuvants is set to a pH of from 5 to 8. The solution is subsequently sterile-filtered.

The examples explain the invention without being restricted thereto.

EXAMPLE 1

Saturation Solubilities of the Oligopeptides with Reference to the Example of Cilengitide In order to determine the saturation solubilities, the oligopeptide was stirred for 1 hour at room temperature in the solvent indicated in each case. The results are shown in Table 1.

TABLE 1

| Formulation | Cilengitide [mg/ml] | pH |
| --- | --- | --- |
| Water for injection purposes | 14.67 | 6.65 |
| Ethanol/water (10% by vol. of ethanol) | 6.68 | 6.63 |
| Ethanol/water (30% by vol. of ethanol) | 3.91 | 6.90 |

TABLE 1-continued

| Formulation | Cilengitide [mg/ml] | pH |
|---|---|---|
| Propanediol/water (10% by vol. of propanediol) | 13.44 | 6.79 |
| Propanediol/water (30% by vol. of propanediol) | 12.54 | 7.01 |
| Propanediol/water (50% by vol. of propanediol) | 8.23 | 7.17 |
| Phosphate buffer pH 1 | 106.10 | 1.23 |
| Phosphate buffer pH 2 | 65.47 | 3.99 |
| Phosphate buffer pH 3 | 22.48 | 4.79 |
| Phosphate buffer pH 5 | 18.64 | 5.50 |
| Phosphate buffer pH 7 | 17.98 | 6.98 |
| 0.9% NaCl solution in water | 19.21 | 6.63 |
| Citric acid/phosphate buffer, pH 2.5 | 83.86 | 3.85 |
| Citric acid/phosphate buffer, pH 3 | 61.89 | 3.98 |
| Citric acid/phosphate buffer, pH 3.5 | 50.03 | 4.24 |
| Citric acid/phosphate buffer, pH 3 with 0.5% of polysorbate 80 VS | 83.19 | 4.14 |
| Citric acid/phosphate buffer, pH 3 with 0.2% Cremophor RH 40 | 73.14 | 4.09 |
| Citric acid/phosphate buffer, pH 3 with 30% of glycerol | 71.48 | 4.33 |
| Citric acid/phosphate buffer, pH 3 with 30% of glycerol and 0.5% of polysorbate 80 VS | 72.67 | 4.32 |

*pH of 80 mg of cilengitide in 20% of 2-hydroxypropyl-β-cyclodextrin: 7.02

The results show that the saturation solubility of the oligopeptide in water was not increased by the addition of the alcohols ethanol and propanediol, but instead was impaired. By contrast, various buffer mixtures in the acidic range produce a significant increase in the saturation solubility. If surfactants are added to acidic solutions with increased solubility for the oligopeptide, this does not result in a further significant increase in solubility. If, instead of or in addition to the surfactants, glycerol is added to the acidic solutions, even a reduction in the solubility is noted.

EXAMPLE 2

Stability of Selected Compositions from Example 1 with High Saturation Solubility for the Oligopeptide Selected compositions in which cilengitide has a high saturation solubility were stored for 8 and 26 weeks at 25° C., 60% r.h. and at 40° C. and 75% r.h. and analysed for their cilengitide content by high-pressure liquid chromatography (HPLC-UV) at the beginning (start) and after the storage time. The results are shown Table 2.

TABLE 2

| Composition | Concentration of cilengitide [mg/ml] | Cilengitide content [%] | | |
|---|---|---|---|---|
| | | Start | 8 weeks 25° C./ 60% r.h. | 26 weeks 40° C./75% r.h. |
| Citric acid phosphate buffer pH 3* | 60 | 98.45 | 66.6 | not measured |
| Citric acid phosphate buffer pH 3 + 0.5% Polysorbate 80 VS* | 60 | 98.43 | 66.77 | not measured |
| Citric acid phosphate buffer pH 2.5* | 60 | 98.57 | 58.07 | not measured |
| Citric acid phosphate buffer pH 3 + 0.2% Cremophor RH 40* | 60 | 98.97 | 67.07 | not measured |
| Citric acid phosphate buffer pH 3, isotonised with NaCl** | 60 | 98.38 | 70.72 | not measured |
| Citric acid phosphate buffer pH 3 + 0.2% Cremophor RH 40, isotonised with NaCl** | 60 | 98.9 | 70.82 | not measured |
| Sodium chloride isotonic* | 15 | 98.87 | 99.2 | 98 |
| Citric acid phosphate buffer pH 7, NaCl** | 15 | 98.8 | 99 | 96.6 |
| NaCl, phosphate buffer pH 7** | 15 | 98.47 | 98.6 | 95 |

*formulation from Table 1
**additional formulation to Table 1

None of the preparations with concentrations of 60 mg/ml of cilengitide exhibits adequate stability. Addition of Cremophor RH 40 or polysorbate 80 VS does not result in better stability compared with the pure buffer solutions. The three tested preparations comprising 15 mg/ml of cilengitide exhibit significantly better stabilities, with the isotonic NaCl solution being the most stable.

EXAMPLE 3

Saturation Solubilities of the Oligopeptides on Addition of β-Cyclodextrin Ethers Analogously to Example 1, the effect of addition of β-cyclodextrin ethers (MS 0.63) on the saturation solubilities of the oligopeptides was determined using the example of cilengitide. The results are shown in Table 3.

TABLE 3

| Formulation | Concentration of cilengitide [mg/ml] | pH |
|---|---|---|
| Water/2-hydroxypropyl-β-cyclodextrin (20%) | >90 | 7.02 (80 mg of cilengitide in 20% of 2-hydroxypropyl-β-cyclodextrin) |
| Water/2-hydroxypropyl-β-cyclodextrin (15%) | >60 | |
| Water/2-hydroxypropyl-β-cyclodextrin (10%) | >40 | |

The results show a significant increase in the solubility of cilengitide through addition of the β-cyclodextrin ethers. In contrast to the additives tested in Example 1, the increase in solubility is directly proportional to the concentration of β-cyclodextrin ether.

EXAMPLE 4

Aqueous preparation comprising:
200 mg of 2-hydroxypropyl-β-cyclodextrin (MS 0.63)
80 mg of cilengitide
to 1 ml of water for injection purposes The stated amount of 2-hydroxypropyl-β-cyclodextrin was dissolved in about 90% of the stated amount of water for injection purposes with stirring, the stated amount of oligopeptide was added, and, after a clear solution had been obtained, the remaining solvent was added. The resultant solution was sterile-filtered, transferred into 6 ml vials each containing 2 ml of solution, sealed with stoppers and crimped.

EXAMPLE 5

Comparative Stability Study of Preparations Comprising an Oligopeptide in Isotonic Saline Solution or in β-Cyclodextrin Ether Solution The preparation in accordance with Example 4 and a preparation prepared analogously comprising 15 mg/ml of cilengitide in isotonic saline solution (0.9% of NaCl) were tested in stability studies. To this end, the aqueous preparations were stored at various temperatures for certain times and analysed using suitable analytical methods. Possible instabilities in the case of oligopeptides in aqueous solution are principally evident from the formation of rearrangement and hydrolysis products. In the case of cilengitide, the decomposition products still carry the same chromophores and, like the starting material, can be determined by HPLC-UV. The results are shown in Tables 4 to 6.

TABLE 4

Stability data at 2-8° C., 26 weeks

| Composition | Concentration of cilengitide [mg/ml] (start) | Cilengitide [%] | Impurity 1 [%]* | Impurity 2 [%] | Impurity 3 [%] |
|---|---|---|---|---|---|
| Isotonic NaCl | 15 mg/ml | 100.67 | 0.48 (start 0.43) | <0.05 | <0.05 |
| 2-Hydroxypropyl-β-cyclodextrin | 80 mg/ml | 99.13 | <0.05 | <0.05 | <0.05 |

*Impurity 1 is specified with max. 2%.

TABLE 5

Stability data at 25° C./60% r.h., 26 weeks

| Formulation | Concentration of cilengitide [mg/ml] (start) | Cilengitide [%] | Impurity 1 [%] | Impurity 2 [%] | Impurity 3 [%] |
|---|---|---|---|---|---|
| Isotonic NaCl | 15 mg/ml | 101.26 | 0.84 (start 0.43) | 0.13 | <0.05 |
| 2-Hydroxypropyl-β-cyclodextrin | 80 mg/ml | 96.56 | 0.39 | 0.14 | <0.05 |

TABLE 6

Stability data at 30° C./60% r.h., 26 weeks

| Formulation | Concentration of cilengitide [mg/ml] (start) | Cilengitide [%] | Impurity 1 [%] | Impurity 2 [%] | Impurity 3 [%] |
|---|---|---|---|---|---|
| Isotonic NaCl | 15 mg/ml | 100.82 | 1.16 (start 0.43) | 0.24 | 0.06 |
| 2-Hydroxypropyl-β-cyclodextrin | 80 mg/ml | 99.37 | 0.74 | 0.25 | 0.08 |

Although the oligopeptide is present in the preparation in accordance with Example 3 in a concentration more than 5 times higher than in the preparation in isotonic saline solution, the preparation in accordance with Example 3 comprising the β-cyclodextrin ether has similar stability to the preparation in isotonic saline solution.

Analytical Test Methods:

Appearance

The preparations prepared were checked visually for particles with the aid of a light source against a dark wall as described in Ph.Eur.

Assay and purity determination of cilengitide

The assay and purity determination was carried out with the aid of an HPLC-UV method at a wavelength of 215 nm. An RP 18 phase was used for the separation. The eluent used was a pH 3.6 buffer consisting of sodium dihydrogenphosphate and phosphoric acid, which was mixed in the same proportion with acetonitrile. A gradient elution with varying proportion of additional acetonitrile was carried out.

The invention claimed is:

1. An aqueous pharmaceutical composition comprising: an oligopeptide of formula I $$\text{cyclo-(n-Arg-nGly-nAsp-nD-nE)} \qquad (I)$$

in which

D and E each, independently of one another, denote Gly, Ala, β-Ala, Asn, Asp, Asp(OR), Arg, Cha, Cys, Gln, Glu, His, Ile, Leu, Lys, Lys(Ac), Lys(AcNH$_2$), Lys(AcSH), Met, Nal, Nle, Orn, Phe, 4-Hal-Phe, homoPhe, Phg, Pro, Pya, Ser, Thr, Tia, Tic, Trp, Tyr or Val;

R denotes alkyl having 1-18 C atoms;

Hal denotes F, Cl Br or I;

Ac denotes alkanoyl having 1-10 C atoms, aroyl having 7-11 C atoms or aralkanoyl having 8-12 C atoms; and n denotes H, R, benzyl or aralkyl radical having 7-18 C atoms on the alpha-amino function of the corresponding amino acid, with the proviso that at least one amino acid has a substituent n, where n denotes R, and where, if the amino acids are optically active, both the D and L forms are included, and physiologically acceptable salts thereof;

and an etherified β-cyclodextrin having a water solubility of greater than 1.8 mg/ml in water.

2. An aqueous pharmaceutical composition according to claim 1, wherein the etherified β-cyclodextrin present is a partially etherified β-cyclodextrin.

3. An aqueous pharmaceutical composition according to claim 1, wherein the ether substituents in the etherified β-cyclodextrin are hydroxymethyl, hydroxypropyl, or combinations thereof.

4. An aqueous pharmaceutical composition according to claim 1, wherein the etherified β-cyclodextrin has a molar degree of substitution of between 0.2 and 10, based on the ether substituents.

5. An aqueous pharmaceutical composition according to claim 4, wherein the partially etherified β-cyclodextrin has a molar degree of substitution of between 0.2 and 2, based on the ether substituents.

6. An aqueous pharmaceutical composition according to claim 4, wherein the partially etherified β-cyclodextrin has a molar degree of substitution of between 0.5 and 0.8, based on the ether substituents.

7. An aqueous pharmaceutical composition according to claim 1, wherein the oligopeptide is cilengitide.

8. An aqueous pharmaceutical composition according to claim 1, further comprising an isotonicity agent in an amount necessary for establishing isotonicity.

9. An aqueous pharmaceutical composition according to claim 1, wherein said composition has a pH of from 5 to 8.

10. An aqueous pharmaceutical composition according to claim 9, wherein said composition has a pH of from 6 to 7.2.

11. An aqueous pharmaceutical composition according to claim 1, wherein said oligopeptide is cilengitide and said etherified β-cyclodextrin is a hydroxypropyl-β-cyclodextrin having a molar degree of substitution of from 0.5 to 0.8, and said composition contains from 20 to 120 mg/ml of cilengitide and from 15 to 25% by weight of said hydroxypropyl-β-cyclodextrin.

12. An aqueous pharmaceutical composition according to claim 11, wherein said composition contains about 80 mg/ml of cilengitide and about 20% by weight of hydroxypropyl-β-cyclodextrin having a molar degree of substitution of about 0.58-0.73.

13. A process for the preparation of an aqueous pharmaceutical preparation according to claim 1, said process comprising:
dissolving the β-cyclodextrin ether in water, and then subsequently adding the oligopeptide and any further adjuvants.

14. An aqueous pharmaceutical composition according to claim 1, wherein said composition has a pH of from 5.6 to 7.4.

15. An aqueous pharmaceutical composition according to claim 1, wherein said composition has a pH of from 6 to 7.2. and the osmolality is from 250 to 350 mOsmol/kg.

16. An aqueous pharmaceutical composition according to claim 2, wherein the ether substituents in the etherified β-cyclodextrin are hydroxymethyl, hydroxypropyl, or combinations thereof.

17. An aqueous pharmaceutical composition according to claim 4, wherein the partially etherified β-cyclodextrin has a molar degree of substitution of 0.58-0.73, based on the ether substituents.

18. An aqueous pharmaceutical composition according to claim 1, wherein said oligopeptide is cyclo-(NMeArg-Gly-Asp-D-Phe-Val), cyclo-(Arg-Gly-Asp-DPhe-NMeVal), cyclo-(Arg-NMeGly-Asp-DPhe-Val), cyclo-(Arg-Gly-NMeAsp-DPhe-Val), or cyclo-(Arg-Gly-Asp-NMeDPhe-Val).

19. An aqueous pharmaceutical composition according to claim 8, wherein said isotonicity agent is a physiologically tolerated salt, physiologically tolerated polyol, or a physiologically tolerated sugar.

20. An aqueous pharmaceutical composition according to claim 19, wherein said isotonicity agent is sodium chloride, potassium chloride, glucose, glycerol or mannitol.

21. An aqueous pharmaceutical composition according to claim 1, further comprising one or more physiologically tolerated adjuvants selected from antioxidants, preservatives, and further stabilisers, structure formers and solubilizers, wherein the stabilisers, structure formers and solubilizers are selected from the group consisting of polyethylene glycols and dextrans.

22. An aqueous pharmaceutical composition according to claim 1, further comprising one or more physiologically tolerated buffers, present in a concentration of from 5 mmol/l to 50 mmol/l.

23. An aqueous pharmaceutical composition according to claim 1, wherein the osmolality is from 250 to 350 mOsmol/kg.

* * * * *

UNITED STATES PATENT AND TRADEMARK OFFICE
CERTIFICATE OF CORRECTION

PATENT NO.        : 7,262,165 B2
APPLICATION NO.   : 10/518924
DATED             : August 28, 2007
INVENTOR(S)       : Hiltrud Lindenblatt It is certified that error appears in the above-identified patent and that said Letters Patent is hereby corrected as shown below:

Column 8, line 36, reads "cyclo-(n-Arg-nGly . . ." should read
--cyclo-(nArg-nGly . . . --
Column 8, line 42, reads "Nal, Nie," should read --Nal, Nle,--
Column 8, line 45, reads "F, Cl Br or" should read --F, Cl, Br or--
Column 9, line 40, reads "from 6 to 7.2." should read --from 6 to 7.2,--

Signed and Sealed this

Fourth Day of November, 2008

JON W. DUDAS
*Director of the United States Patent and Trademark Office*